United States Patent [19]

Tayot et al.

[11] Patent Number: 5,436,135
[45] Date of Patent: Jul. 25, 1995

[54] NEW PREPARATION OF PLACENTA COLLAGEN, THEIR EXTRACTION METHOD AND THEIR APPLICATIONS

[75] Inventors: Jean-Louis Tayot, La Tour de Salvagny; Michel Tardy, Lyons, both of France

[73] Assignees: Pasteur Merieux Serums et Vaccins; Imedex, both of France

[21] Appl. No.: 638,022

[22] Filed: Jan. 7, 1991

Related U.S. Application Data

[63] Continuation-in-part of Ser. No. 901,429, Aug. 28, 1986, abandoned.

[30] Foreign Application Priority Data

Sep. 2, 1985 [FR] France .................. 85 13004

[51] Int. Cl.⁶ ........................... C07K 14/78
[52] U.S. Cl. .................... 435/68.1; 530/356
[58] Field of Search ............ 435/68.1, 267, 268, 435/272, 273; 530/356, 412, 418, 419, 420, 422, 427, 851

[56] References Cited

U.S. PATENT DOCUMENTS

| | | | |
|---|---|---|---|
| 3,949,073 | 4/1976 | Daniels et al. | 514/2 |
| 4,264,155 | 4/1981 | Miyata | 530/356 |
| 4,295,894 | 10/1981 | Cioca et al. | 530/356 |
| 4,505,855 | 3/1985 | Bruns et al. | 530/356 |

OTHER PUBLICATIONS

Glanville et al., "Isolation and Characterization of a Native Placental Basement-Membrane Collagen and its Component & Chains" Eur. J. BioChem V95,383–389.

Sage et al, "Structural Studies on Human Type IV Collagen" J. Biological Chemistry, V254(9), 9893–9900, 1979.

Rauter et al, "Wound Healing Composition Containing Collagen from Basal Membranes" Chem Ab. V.98(24): 204394q, 1983.

Kresina et al, "Isolation and Characterization of Basement Membrane Collagen from Human Placental Tissue, Evidence for the Presence of Two Genetically Distinct Collagen Chains", Biochemistry V18(14) 3089–3097, 1979.

Isemura et al, "Thermoreversible Sol–gel transformation of Collagen Solution" Chem. Abstracts V.92(17) 142029g, 1979.

Ivanova et al, "Collagen Solutions" Chem. Abstracts, V.102(2), 12366m, 1984.

Primary Examiner—Howard E. Schain
Attorney, Agent, or Firm—Larson and Taylor

[57] ABSTRACT

Human or animal placenta is subjected to moderate enzymatic digestion, in particular with pepsin at an acid pH, then, after separation of the residual tissue the impurities are separated at a moderately acid pH, the collagen is precipitated at a neutral pH, redissolved and the residual impurities precipitated at an acid pH. The collagen obtained can be brought back to a neutral pH and dried in the form of fibres. Completely transparent, physiological and hemocompatible gels and solutions can be prepared. Applications for the fabrication of contact lenses and implants.

15 Claims, No Drawings

NEW PREPARATION OF PLACENTA COLLAGEN, THEIR EXTRACTION METHOD AND THEIR APPLICATIONS

This application is a continuation-in-part of U.S. application Ser. No. 06/901,429 filed Aug. 28, 1986, now abandoned.

This invention relates to the preparation of a gel or a physiological solution from unmodified, transparent and hemocompatible collagen derived from placenta.

In general it covers a method for the extraction of collagen from human and animal placenta enabling type IV enriched collagen to be isolated and used industrially.

It relates more precisely to a method for the preparation of acid or neutral collagen solutions or gels that are completely transparent at a great thickness.

Attempts have been made for a number of years to develop transparent collagen gels for the fabrication of contact lenses, More recently their utilization has been sought for grafting to or inserting these products in the cornea itself, and even in the eye. The importance of having a collagen identical with human collagen or as near to it as possible for surgical use in the human species will be understood if any inflammatory or immunological reaction is to be avoided. But today the only collagen preparations available in commerce in sufficient quantity and at an acceptable price are those obtained from rat tails or tendons or from the skins of young animals (calf, for example). They consist almost solely of type I collagen. The other types, II, III, IV, V and others are prepared only by specialized research workers at prices that are too high to allow their being used on a large scale.

It has been stated in numerous publications that animal collagen molecules are not very antigenic or not antigenic when they are obtained by a method using pepsin which removes the non-helical terminal peptides (teloptides). The triple helix structure of collagen, resistant to the action of pepsin, being similar in all animal species is said to be not very antigenic. But, it seems that this non-antigenic character of collagen that has been subjected to the action of pepsin must be involved. For it is now known that these structures are antigenic in an other species, which has enabled specific antisera to be prepared from a particular or other type of bovine or human collagen, in the rabbit for example. In addition, account must be taken of the always possible presence of antigenic animal protein impurities in such preparations.

Since some years ago the injection of collagen I of bovine origin has been practiced intensively in the human species to close up scars or in repair surgery techniques. These tests revealed a number of disadvantages of which two are important:
the occurrence of immunological reactions in 1 to 3 % of subjects,
the occurrence of local blood coagulation reaction as when the product has unfortunately been injected into a blood vessel or capillary.

These facts therefore underline how very important it would be to obtain human collagen gels which were not only transparent for use in ophthalmology in the human species without risk of any occurrence of undesirable immunological reactions but also hemocompatible and physiological.

Type I, II or III human or animal collagens, even after the action of pepsin, have a characteristic fibrillar structure under an electron microscope, which make them powerful platelet aggregating agents. But as these collagens are not hemocompatible, it is preferable to avoid using them whenever the physician concerned .does not require a contact coagulant effect.

Since these collagens are practically insoluble at a neutral pH, only opaque suspensions can be obtained and it is impossible to use them for the preparation of transparent, physiological gels (isotonic at a neutral pH), without chemically modifying the collagen molecules resulting in the appearance of antigenic determinants. U.S. Pat. No. 3,553,299, THIELE, has already described the fabrication of contact lenses with a gel obtained from the crystalline lens of the eye, and consisting therefore essentially of collagen. U.S. Pat. Nos. 4,223,984 and 4,268,131, MIYAYA, also deal with the fabrication of contact lenses from a type I collagen gel which, to be soluble at a neutral pH, must be modified chemically.

The methods described in these patents give relatively transparent gels of only snail thicknesses that are not very strong mechanically. It is not clear when reading them whether the transparency is obtained because of a subsequent chemical conversion (succinylation or methylation).

U.S. Pat. No. 4,388,428, KUZMA, describes gels in which the collagen is mixed with chemical polymers to improve their chemical properties. The use of such products is not desirable because of the difficulties in removing all traces of toxic products from viscous or solid gels.

R. R. BRUNS and J. GROSS (U.S. Pat. No. 4,505,855) confirm the difficulty of obtaining completely transparent gels from animal collagen by prior art methods. They suggest an ultra-centrifuging method, but this method is very costly and difficult to reconcile with industrial usage.

In addition, consideration has already been given to enzymatic extractions of placenta collagen with pepsin, but the collagen preparations obtained do not have the transparency properties required for use in the field of ophthalmology.

Thus M. Z. ABEDIN and R. RIEMSCHNEIDER (Die Angewandte Makromoiekulare Chemie, Vol . 11, No. 1701 January 1983, pages 107–122, Hüthig & Wepf Verlag, Heidelberg) describe a method for the digestion of placenta with pepsin which results in the contamination of type IV collagen by types I and III, requiring precipitation and redissolution at a high NaCl concentration indicating the intensive character of the digestion.

These same authors (Die Angewandte Makromolekuiare Chemie, Vol. 82, No. 1276, 1979, pages 171–186) describe a method for a long-duration treatment of placenta with ether, followed by freeze-drying and then treatment with sodium acetate or caustic soda before digestion with pepsin and then dialysis of the supernatant layer in order to precipitate collagen. The collagen, after having been taken up, must also be precipitated at a high NaCl concentration. These conditions, which moreover preclude application on an industrial scale, also bear witness to the excessively intensive character of the digestion and the non-transparent product obtained appears to be especially type I+III collagen.

Th. F. KRESINA and Ed. J. MILLER (isolation and characterization of basement membrane collagen from human placental tissue. Evidence for the presence of two genetically distinct collagen chains. Biochemistry, Vol. 18, No. 14, 1979, pages 3089–3097, American Chemical Society) also describe a total pepsin digestion of placental tissue resulting in heavy contamination by type I and III collagens. After fractionation, the collagen must be treated at an acid pH at high NaCl concentrations. The product obtained is not suitable for ophthamological uses.

German Patent Application 2,462,222 describes a pepsin treatment consisting of successive extractions of the supernatant layer of placental tissues giving a cloudy solution of collagen.

European Patent Application 0,080,956 describes a pepsin digestion of alkaline extracts of placenta giving an opaque, denatured collagen.

H. Sage and al. (J. of Biol. Chem. Vol. 254 NO. 19, 1979, 9893–9900) state that a major difficulty associated with most studies of the type IV collagens has been the extreme insolubility of these proteins. They therefore need a pepsin digestion of the protein conducted to obtain small collagen chains of 140, 100 and 70 kilodaltons. This strong digestion leads to a loss of collagenous starting material and to very fluid solutions which are not adapted for use in the field of ophthalmology.

The object of this invention is to overcome these various disadvantages by providing unmodified, non-antigenic, completely transparent physiological and hemocompatible preparations of collagen free from striated fibres observable under an electron microscope, it being possible to provide these preparations in the form of gel or solution.

These preparations are advantageously enriched with type IV or even contain essentially type IV collagen.

The collagen solutions or gels obtained are transparent in great thicknesses, capable easily of attaining 20 mm, a thickness which is largely sufficient to meet the needs of the market (contact lenses, intra-ocular or corneal implants).

An extraction method has been developed by the applicant starting from human placenta, the only source that can be considered for the preparation of human collagen on an industrial scale.

The knowledge of this new method suitable for human placenta has enabled the applicant to extend it to animal placentas. For animal collagens can be useful in veterinary medicine, for example, or acceptable for use as a non-implanted external device in man such as contact lenses.

The method according to the invention consists therefore:
first, in extracting collagens from human and animal placenta and then isolating a type IV enriched collagen;
secondly, in preparing solutions or gels from this type IV enriched collagen having the previously described properties.

The method for the extraction of placenta collagens according to the invention is characterized in that it comprises the following steps:
starting with human or animal placenta in deep-frozen form and grinding it;
washing the ground placental tissue, for example, by successive washings at a neutral pH and then at an acid pH;
subjecting said placental tissue to enzymatic digestion in order to extract type IV collagen, practically uncontaminated by type I or III collagens. Digestion is carried out with a suitable enzyme (with the exception of collagenase), preferably pepsin. In that case, digestion is preferentially carried out at an acid pH, preferably between 2 and 3.5 at a temperature preferably of between 0° and 20° C. for a suitable time, in particular of the order of 8 to 24 h, the quantity of pepsin per kg of deep-frozen placenta being between 0.5 and 2 g, preferably between 0.5 and 1 g or 1.5 g.

The tissue residue having resisted the first treatment may if necessary be subjected to a second digestion with pepsin, this second digestion being carried out under the same conditions as the first digestion, enabling type I and type III collagens practically free from type IV collagen, to be recovered subsequently by known methods.

The placenta suspension having undergone the first enzymatic digestion is then treated by the following method, consisting successively:
after separating the residual tissue from the placenta suspension derived from the enzymatic digestion,
in precipitating at a moderately acid pH to remove a precipitate of impurities,
precipitating the collagen from the supernatant layer by precipitation with a salt at a neutral pH,
redissolving the precipitated collagen and neutralizing the solution obtained,
removing the insoluble impurities, and
precipitating the collagen with a salt at an acid pH.

Thus the placenta suspension derived from the enzymatic digestion can advantageously be subjected to the following steps:
diluting said suspension, in particular by a volume of water;
adjusting the pH to a value between 7 and 9 or 10;
allowing said suspension to rest for 1 to 24 hours at a temperature of between 0° and 20° C.;
separating the residual tissue from the supernatant layer of the first digestion;
adjusting the supernatant layer to a moderate pH, for example, of between 4.5 and 5.5;
allowing said supernatant layer to rest, for example, for 1 to 24 h at a temperature between 0° and 20° C.;
removing the insoluble part containing numerous impurities;
adjusting the clear supernatant layer to an about neutral pH of the order of 7.5;
adding a salt, such as for example NaCl, until a final concentration of about 1.2 M is obtained;
allowing the suspension obtained to rest, for example, for 1 to 24 h at a temperature between 10° and 25° C.;
recovering the collagen precipitate formed;
dissolving the precipitate in a weakly acid solution;
neutralizing the solution to a pH of 7.5;
allowing the suspension obtained to rest for 1 to 24 hours at a temperature between 0° and 20° C.;
removing the insoluble part, thereby also removing the impurities that might affect transparency adversely:
acidifying the supernatant layer to an acid pH of, for example, between 2 and 3.5 or 4;

precipitating the collagen with a salt, such as NaCl, until a final concentration of between 0.4 and 0.8 M is obtained;

allowing the suspension obtained to rest for 1 to 24 h at a temperature of between 0° and 25° C.;

recovering the precipitate of purified acid collagen.

The purified collagen precipitate obtained on completion of the operation is taken up with acetone or an equivalent volatile organic solvent, which results in the formation of acid collagen fibres that are recovered by filtration through a sieve. These fibres are dried under a current of lukewarm, sterile air.

By fibres are here understood to mean the appearance the solid collagen assumes after drying, and which in no way corresponds to the striated fibrous structure as such observable under an electron microscope with known collagens in solution.

In a variant of the embodiment of the invention, the purified collagen precipitate is redissolved in water. The pH of the solution is adjusted to 7.5 and a salt, such as NaCl, added to it until a final concentration of the order of 1.2 M is obtained. The suspension obtained is allowed to rest for 1 to 24 h and the neutral collagen precipitate recovered.

The precipitate of neutral collagen fibres obtained is taken up with acetone or an equivalent volatile organic solvent, which results in the formation of neutral collagen fibres which are recovered by filtration through a sieve. These fibres are dried under a current of lukewarm, sterile air.

It is these acid or neutral collagen fibres in their dry state (<10 %) which are used as a source of collagen for the preparation of solutions or gels according to the invention.

Gels from acid or neutral collagen fibres obtained after treatment with acetone can be prepared as follows:

the fibres are brought into contact with a volume of water determined so as to obtain a collagen concentration of between 2 and 30 %;

the fibres are allowed to swell in the water, for example, for 1 h;

the whole is subjected to moderate heating;

the viscous, transparent solution is filtered through membranes of pore size between 0.2 and 8µ;

the solution is allowed to cool.

A solution of collagen from type IV enriched acid collagen fibres is prepared by the following method:

the collagen fibres are brought into contact with a determined volume of water;

the collagen fibres are allowed to swell in the water, for example, for about 1 h;

a solution of a salty such as for example, sodium acetate at a concentration of less than or equal to 0.1M is added to initiate neutralization.

The volumes of water are determined so as to obtain collagen concentration of at the most 2 %.

the solution is adjusted to a pH of about 7.5 and if necessary made isotonic by addition of NaCl;

- the solution is subjected to moderate heating at a temperature of between 30° and 80° C. for 10 to 60 minutes. As a variant, the collagen solution may be filtered in the acid state through membranes of pore size between 0.2 and 8µ. Neutralization takes place only after this, if necessary under bacterially sterile conditions, to ensure that the product prepared is sterile, while facilitating the filtration operation as a collagen solution is less viscous at an acid pH. Another variant consists in filtering the solution while subjecting it to ultrasonic vibrations to reduce the viscosity temporarily.

the solution is filtered through membranes of pore size between 0.2 and 8µ;

and the solution allowed to cool.

On completion of these operations a solution is obtained which has these characteristics:

it is very viscous, it contains at the most 2 % of non-denatured, collagen, it is completely transparent, it is isotonic, physiological and hemocompatible, it is free from striated fibres visible under an electron microscope.

Such a solution may be used as an implant in human and animal medicine, in the fields of ophthalmology, bone joints, treatment of burns and dermatology.

When acid collagen fibres are no longer used as a source of collagen but neutral type IV enriched neutral collagen obtained according to a variant of the embodiment of the invention, the same successive operations as those previously described are performed to obtain solutions from collagen fibres, neutralization no longer being necessary.

To prepare a collagen solution from type IV enriched neutral collagen fibres, the following procedure is followed:

the neutral collagen fibres are dissolved in a volume of water determined so as to obtain a collagen concentration of at the most 2%;

to this solution is added a salt such as NaCl until a concentration of the order of 0.15M is obtained;

said solution is subjected to moderate heating at a temperature of between 30° and 80° C. for 10 to 60 minutes, preferably at a temperature of about 60° C. for some ten minutes;

the solution is filtered through membranes of pore size between 0.2 and 8µ;

and the solution allowed to cool.

A solution is obtained which has the same characteristics as the collagen solutions prepared from acid collagen.

Other advantages and features of the invention will become apparent on reading the non-limitative examples of embodiment of the invention given hereinafter.

Example 1 illustrates the method for the extraction of type IV enriched collagen from human placentas and the preparation of acid collagen fibres.

Example 2 relates to the preparation of neutral collagen fibres according to the invention.

Example 3 illustrates the method for the extraction of type IV enriched collagen from animal placentas.

Examples 4 and 5 describe the preparation of 15 % collagen gels.

Examples 6, 7, 8 and 9 describe the preparation of collagen solutions.

EXAMPLE 1

300 kg of deep-frozen placenta were ground to give lumps of a few cm$^3$. The ground material was then mixed with 300 l of an aqueous solution containing 8 % ethanol, 6 g/l of NaCl and 10 kg of cellulose After stirring at 10° C. the whole was pressed in a MABILLE press to separate the blood from the placental tissue. 102 kg of placental tissue containing 65 % water were obtained.

The tissue extracted from the press was stirred in 500 l of 0.05M sodium citrate at a pH of 7.2 for 30 minutes at 10° C. and then pressed to remove the washing solution and recover the tissue. A second washing operation was performed with 500 l of 0.05M sodium citrate at a pH of 7.2 with addition of 30 g/l of NaCl. A third washing operation was performed with 500 l of 0.05M of sodium citrate at a pH of 7.2. The tissue washed in this way at a neutral pH was then subjected to three successive washing sequences at an acid pH at 10° C.:

- with 500 l of 0.05M citric acid at a final pH adjusted to 2.8 by addition of 2N HCl; stirring for 30 minutes before the pressing operation;
- with 500 l of 0.5M formic acid for 15 h;
- with 500 l of 0.05M citric acid for 30 mn, with addition of 20 g/l.

The placental tissue washed in this way has a white appearance which is evidence of a good removal of the red pigments from the initial placental blood. The weight obtained was 82 kg.

It was then subjected to enzymatic digestion with pepsin in 500 l of 0.05M citric acid at a pH of 2.8 containing 300 g of pepsin for 15 h at 10° C. The suspension was then diluted by addition of 500 l of water at 10° C. The pH was adjusted to 7.5 by addition of 4 N NaOH in order to denature the pepsin and suppress its protease action. After a waiting period of 15 h at 10° C. the tissue residue which contained the essential of the non-solubilized collagens I and III was separated continuously by means of a centrifuge (Westfalia KG 10006). The weight of this residue was 103 kg; it could be subjected to a second enzymatic digestion identical with the first one, followed by extraction and separation of each of the collagens I and III by the methods described in the literature.

The supernatant layer corresponding to the first enzymatic digestion contains the essential of the collagens and other macromolecules soluble at a neutral pH after action of the pepsin. In particular it contains type IV collagen.

The pH of the supernatant layer was adjusted to 5 with 2N HCl and, after a waiting period of 15 h at 10° C. the precipitate formed removed by continuous centrifuging in an Alfa Laval "Bactofuge" centrifuge.

The pH of the supernatant layer, which was very clear, was adjusted to 7.5 by addition of 4N NaOH and at a final concentration of 1.2 M in NaCl. After 15 h at 16° C., the collagen precipitate formed was recovered by continuous centrifuging in a "Bactofuge" centrifuge.

The precipitate of 13 kg was then dissolved in 600 l of 0.01N HCl and the pH adjusted to 7.5 by addition of 4N NaOH. The precipitate formed after a waiting period of 15 h at 4° C. was removed in the "Bactofuge" centrifuge (weight obtained 10 kg).

The clear supernatant layer was acidifed to a pH of 2.8 with 2N HCl until a final concentration of 0.6M was obtained at 4° C.

After 15 h, the collagen precipitate was collected in a "Bactofuge" centrifuge. The precipitate whose weight was 6.5 kg had a fluid aspect. 7 l of acetone were gradually added to it, which resulted in the formation of collagen fibres that were recovered by filtration through a sieve. Washing these fibres by several treatments with acetone gave, after drying under a lukewarm, sterile current of air, 180 g of dry fibres of final product. The analysis of the composition of the amino acids of these fibres showed a structure similar to that of type IV collagen and characteristic of the collagen family ($\geq$ 30 % glycine, about 10 % glutamic acid, proline and hydroxyproline).

The following Table snows the results of the analysis of the composition of the amino acids of four different preparations of human placenta collagen obtained by application of the method given in this example (the results are expressed in numbers of molecules of each acid per 1000 residues ).

| Batch No | 1022 | 1023 | 1025 | 1027 |
|---|---|---|---|---|
| ASP | 46 | 42 | 41 | 42 |
| HYP | 80 | 91 | 85 | 86 |
| THR | 19 | 18 | 18 | 18 |
| SER | 17 | 15 | 17 | 16 |
| ASN | 28 | 30 | 31 | 25 |
| GLU | 107 | 105 | 105 | 107 |
| GLN | 3 | traces | 1 | traces |
| PRO | 92 | 91 | 96 | 98 |
| GLY | 317 | 327 | 313 | 324 |
| ALA | 41 | 39 | 39 | 43 |
| VAL | 33 | 29 | 34 | 34 |
| CYS | 9 | 6 | 9 | 6 |
| CYSTA | 1 | 1 | 1 | 1 |
| MET | 15 | 26 | 16 | 16 |
| ILE | 36 | 36 | 37 | 36 |
| LEU | 57 | 56 | 57 | 56 |
| TYR | 10 | 7 | 12 | 10 |
| PHE | 33 | 31 | 39 | 34 |
| ORN | 3 | 1 | 1 | 1 |
| LYS | 9 | 8 | 12 | 12 |
| TRY | 0 | 0 | 0 | 0 |
| HIS | 8 | 8 | 8 | 8 |
| ARG | 32 | 32 | 28 | 27 |
| Total | 999 | 996 | 1000 | 1000 |

The experimental determination of the molecular weight and viscosity characteristics of collagen IV obtained in example I leads to the following results, where FIG. 1 represents the electrophorectic profile:

a) Apparent Molecular Weights

Analysis of electrophoretic curves for denaturation compounds as obtained with 16 batches of Type IV collagen and calculation of apparent molecular weights according to globular protein standards (COMBI-THEK$^R$ Kit Ref. 750115, Boehringer, Mannheim) yield the following results, without taking into account the considerable amounts of aggregates not penetrating into the gel, with or without a reducing agent.

* While the sample has not been reduced a set of bands corresponding to apparent molecular weights can be seen as traces in an interval between 100,000 and 165,000.

* After reduction, one obtains electrophoretic bands which correspond to the following apparent molecular weights (values for the main 6 bands only were calculated):

Band 1: 326,000
Band 2: 207,500
Band 3: 176,000
Band 4: 158,000
Band 4': 143,000
Band 5: 111,000 b) Determination of Theoretical Effective Molecular Weights

Collagen proteins' mobility on electrophoresis is lower than that of globular proteins on polyacrylamide gel electrophoresis in the presence of SDS. Thus the collagen's apparent molecular weight is about 26% higher than its effective molecular weight (BUTKOWSKI et al., 1982).

Apparent molecular weights as given above must thus be corrected so as to obtain an approximate effective molecular weight. Corrections are made taking into account apparent and effective values of Type I collagen standard:

| | * Type I collagen | | |
|---|---|---|---|
| Band s | apparent MW | Eff. MW (DEYL et al., 1981) | Calc. corr. coeff. |
| α 1 (I) (α2 (I)) | 135,000 (115 000) | 95,1000 | 0.704 |
| β 11 (β 12) | 250,000 (225,000) | 190,000 | 0.760 |

| | * Type IV collagen (and COLLAGEL ®) | | |
|---|---|---|---|
| Band s | Aver. appar. MW as obt. with several batches of Type IV coll. | Theoretical calculated MW | Corr. coeff. used |
| 1 | 326,000 | 248,000 | 0.760 |
| 2 | 207,500 | 158,000 | 0.760 |
| 3 | 176,000 | 134,000 | 0.760 |
| 4 | 158,000 | 120,000 | 0.760 |
| 4' | 143,000 | 100,000 | 0.704 |
| 5 | 111,000 | 78,000 | 0.704 | c) Comparison with Literature Data (See FIG. 1)

Analysis of effective molecular weights (calculated as a function of Type I collagen standard) yields the following results:

* Without reduction of Type IV collagen:

a very high intensity band at the starting point of the gathering gel (Stacking), demonstrating the presence of macromolecules with an apparent molecular weight of 410,000 or above, including macromolecules of about 1000 kD;

a set of very low intensity bands migrating to the level of the α bands and in positions slightly above or under them;

* After reduction of Type IV collagen:

the highly intense band at the starting point of the gathering gel persists and corresponds to compounds having very high molecular weights, partially agglutinated by covalent bridges, and which do not penetrate into the polyacrylamide gel. This band forms at least 10% of the total collagen weight;

bands corresponding to high molecular weights at the level of the collagen standard compounds;

bands which have migrated between the reference α and β bands of Type I collagen: 170,000 / 140,000 /120,000;

at the α1 band level (I) : 95,000 below the α2 band level (I) : 70,000

The presence of high intensity bands not penetrating the polyacrylamide gel before reduction or partially penetrating it after reduction must be emphasized. These bands show the presence of high molecular weight aggregates including the 7 S area with the disulfide bridges which are reduced by the use of mercaptoethanol.

As already noted these very mild peptic solubilization conditions allow:

the existence of these very high molecular weight aggregates, which are essential for obtaining an optimal viscosity of Type IV collagen solutions (at or above 10 Pascal.sec), as measured with a fixed speed gradient of 4 revolutions per second.

the presence of cleavage products also having high molecular weights : 170,000 , 140,000 .....

EXAMPLE 2

The method described in Example 1 was applied in a strictly identical manner to a second batch of 300 kg of human placentas.

On completion or this operation, the weight of the precipitate obtained at a pH of 2.8 in the presence of 0.6 M NaCl at 4° C. was 6.5 kg. This precipitate was redissolved in 200 l of water. The pH of the solution obtained was adjusted to 7.5 by addition of 4 N NaOH at +16° C. and NaCl added to obtain a final concentration of 1.2 M.

The precipitate formed after 15 h was recovered by centrifuging in a "Bactofuge". The weight obtained was 3450 g. The precipitate, dried with acetone as in Example 1, gave 200 g of dry neutral collagen fibres, enriched essentially with type IV collagen.

EXAMPLE 3

The method described in Example 1 was applied in a strictly identical manner to 180 kg of cow placentas. Successive washings were carried out with volumes of 300 litres. The first digestion with pepsin was carried out by addition of 180 g of pepsin in 300 l of 0.05 M citric acid adjusted to a pH of 2.8. The other selective collagen precipitation steps were identical with those of Example 1.

After final drying with acetone, 130 g of dry bovine collagen fibres were recovered. An analysis by polyacrylamide gel electrophoresis in the presence of sodium dodecyl sulfate (SDS) with or without reductant (dithiothreitol) demonstrated that this preparation was rich in type IV collagen.

Dissolution of these bovine collagen fibres in water gave an acid solution due to the final precipitation being made to take place at an acid pH.

EXAMPLE 4

1.5 g of dry, human collagen fibres prepared according to Example 1 were brought into contact with 10 ml of distilled water. After the fibres had swelled for 1 h, the whole was placed in a water-bath at 70° C. for 30 minutes. A very viscous, transparent solution was obtained which could be filtered easily through membranes of pore size between 0.8 and 8μ at this same temperature. After cooling, the gel obtained was colourless, acid and completely transparent, like filtered water.

Checks by polyacrylamide gel electrophoresis in the presence of sodium dodecyl sulfate with or without dithiothreitol demonstrated the complete preservation of the collagen IV molecules during the heating stage.

This gel could then be subjected to known operations of shaping into contact lens forms or any other device with optical properties. Moulding and cross-linking methods by chemical agents (aldehydes) or physical agents (γ,β, X-ray or UV radiation) can be applied perfectly well.

EXAMPLE 5

The bovine collagen fibres prepared according to Example 3 were dissolved according to the protocol in Example 4. A gel with physical properties comparable to that of Example 4 was obtained.

EXAMPLE 6

1 g of neutral collagen fibres obtained in Example 2 were dissolved in 90 ml of distilled water. To the final solution of pH 7.5 adjusted to 100 ml was added sodium chloride so as to obtain a final concentration of 0.15M taking the sodium chloride already present in the initial precipitate into account.

The solution obtained contained about 1% protein, principally type IV human collagen.

Placed in a water-bath at 60° C. for 10 minutes, this solution could be filtered through membranes of pore size between 0.2 and 8μ. Filtration could be facilitated by subjecting the solution to ultrasonic vibrations. After cooling, a very viscous, completely transparent, sterile solution of human collagen was obtained.

This solution was hemocompatible. Thus after dilution in nine volumes of human blood drawn off over citrate, it did not cause any blood coagulation, platlet aggregation, or activation of prothrombin into thrombin.

EXAMPLE 7

1 g of human collagen fibres prepared according to Example 1 were placed in 50 ml of water to swell for 1 h and 50 ml of 0.1M of sodium acetate added. The final solution obtained contained about 1% of proteins, principally type IV human collagen. Its pH was adjusted to 7.5 and if necessary the solution could be made isotonic by addition of sodium chloride.

Placed in a water bath at 60° C. for 10 minutes, this solution could be filtered through membranes of pore size between 0.2 and 8μ. A very viscous, physiological, completely transparent, sterile solution of human collagen was obtained.

This solution, like the preceding one, was hemocompatible.

EXAMPLE 8

The method described in Example 7 was repeated in exactly the same manner with the exception of the addition of 50 ml of 0.1M sodium acetate, which was replaced by the addition of 50 ml of 0.05M disodium phosphate.

The solution obtained was hemocompatible.

EXAMPLE 9

1 g of collagen fibres prepared according to Example 1 were placed in 50 ml of water to swell for 1 h. The solution obtained was heated for 10 mn at 30° C. and filtered through membranes of pore size 0.2μ.

The use of ultrasonics can accelerate such filtration, as also heating to 37° C. To the sterile solution obtained were then added 50 ml of 0.1M sodium acetate. The pH was adjusted to 7.5 with addition if necessary of sodium chloride to obtain a physiological aqueous solution. All these operations after filtration may be performed protected from bacterial contamination.

A solution identical with the preceding solutions was obtained.

What is claimed is:

1. A method for extraction of placenta collagens in which the placenta is digested enzymatically, characterized in that starting with human or animal placenta in deep-frozen form which is ground and washed:
   the washed placental tissue is subjected to enzymatic digestion, said digestion being carried out with pepsin at an acidic pH, at a temperature between 0° C. and 20° C. for a time between 8 and 24 h. the pepsin content with respect to the deep-frozen placenta being between 0.5 and 1.5%,
   said suspension is diluted with a volume of water,
   the pH is adjusted to between 7 and 10,
   said suspension is allowed to rest for 1 to 24 h at a temperature of between 0° and 20° C.,
   the residual tissue is separated from the supernatant layer,
   the residual tissue containing the non-solubilized type I and type III collagens whereas the supernatant contains type IV collagen is practically free from type I and type III collagens,
   precipitation is made to take place in the supernatant layer at a moderately acidic pH of 4.5–5.5 to remove a precipitate of impurities, the supernatant layer is collected and the collagen it contains is precipitated by precipitation with a salt at a neutral pH, the precipitated collagen is redissolved in a weakly acid solution which is neutralized, the insoluble impurities are removed, and the collagen is precipitated by acid precipitation with salt.

2. A method according to claim 1, characterized in that the placental tissue residue having resisted the first treatment with pepsin is subjected to a second digestion, this second digestion being carried out under the same conditions as the first digestion, enabling type I and type III collagens practically free from type IV collagen to be recovered subsequently.

3. A method according to claim 1, characterized in that for precipitation to take place at a moderately acid pH of about 4.5–5.5:
   the residual tissue is separated from the supernatant layer of the first digestion,
   the pH of the supernatant layer is adjusted to a pH of between 4.5 and 5.5,
   said supernatant layer is allowed to rest for 1 to 24 h at a temperature of between 0° and 20° C., and
   the insoluble part removed.

4. A method according to claim 1, characterized in that for precipitation with a salt to take place at a neutral pH,
   the pH of the supernatant layer is adjusted to 7.5,
   a salt is added until a concentration of 1.2M is obtained,
   said supernatant layer is allowed to rest for 1 to 24 h at a temperature of between 10° and 25° C.,
   the collagen precipitate formed is recovered.

5. A method according to claim 1, characterized in that in order to remove the impurities,
   the precipitate is dissolved in a weakly acid solution,
   the solution is neutralized to a pH of 7.5,
   said solution is allowed to rest for 1 to 24 h at a temperature of between 0° and 20° C.,
   the insoluble part is removed.

6. A method according to claim 1, characterized in that to precipitate the purified collagen,
   the supernatant layer is acidified to a pH of between and 3.5 to 4,
   the collagen is precipitated with a salt, until a final concentration of between 0.5M and 0.8M is obtained,
   the solution is allowed to rest for 1 to 24 h at a temperature of between 0° and 25° C.,
   the purified collagen precipitate is recovered.

7. A method according to claim 1, characterized in that precipitate of purified collagen is redissolved,
   the collagen is precipitated with a salt at a neutral pH.

8. A method according to claim 7, characterized in that:
- the final precipitate of purified acid collagen is redissolved in water,
- the pH of the solution is adjusted to neutral,
- a salt, is added to the solution until a concentration of 1.2M is obtained,
- the solution is allowed to rest for 1 to 24 h, and
- the collagen precipitate formed is recovered, said precipitate being a source of purified collagen for the preparation of solutions or gels.

9. A method according to claim 1, characterized in that:
- the acid or neutral purified collagen precipitate is taken up with a volatile, organic solvent, which results in the formation of collagen fibres,
- said fibres are recovered and dried, to provide a source of purified collagen for the preparations of solutions or gels.

10. A method according to claim 9, characterized in that collagen gels are obtained:
- by bringing the collagen fibres into contact with a volume of water determined so as to obtain a collagen concentration of between 2 and 30 %,
- by allowing said fibres to swell,
- by subjecting said fibres to moderate heating at a temperature of between 30° and 80° C. for 10 to 6 minutes, preferably of about 70° C. for about thirty minutes,
- by filtering the transparent, viscous solution obtained through a membrane of pore size between 0.8 and 8μ,
- and allowing said solution to cool.

11. A method according to claim 9, characterized in that collagen solutions are obtained:
- by bringing the collagen fibres into contact with a volume of water,
- by allowing said fibres to swell in the water,
- by adding a solution of a salt, such as sodium acetate, at a concentration of tile order of 0.1M, the volumes of water being determined so as to obtain a collagen concentration at the most equal to 2 %,
- by adjusting the pH to about 7.5,
- by subjecting said solution to heating at a temperature of between 30° and 80° C. for 10 to 60 minutes,
- by filtering said solution through membranes of pore size between 0.2 and 8,
- then cooling said solution.

12. A method according to claim 9, characterized in that the collagen solutions are obtained:
- by dissolving the collagen precipitate in a volume of water determined so as to obtain a collagen concentration at the most equal to 2 %,
- by adding a salt, to the solution until a concentration of the order of 0.15M is obtained,
- by subjecting said solution to moderate heating, at a temperature of between 30° and 80° C. for 10 to 60 minutes, preferably at about 60° C. for about 1 minute,
- by filtering the solution through membranes of pore size between 0.2 and 8μ,
- allowing said solution to cool.

13. A method according to claim 10, characterized in that the solution is subjected to ultrasonic vibrations during filtration.

14. Transparent collagen gel obtained from human or animal collagen enriched with type IV collagen or consisting essentially of type IV collagen, characterized in that it comprises between 2 to 30% of collagen which is non-denaturated, unmodified, completely transparent, free from striated fibers visible under an electron microscope, and soluble in both acid solutions and physiological saline solutions.

15. Transparent collagen gel according to claim 14, wherein the collagen is obtained according to the method of claim 10.

* * * * *